(12) United States Patent
Halpern

(10) Patent No.: US 6,510,344 B1
(45) Date of Patent: Jan. 21, 2003

(54) PROCEDURE ALARM SILENCE FEATURE FOR MEDICAL TELEMETRY SYSTEM

(75) Inventor: Arieh S. Halpern, Beverly Hills, CA (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 0 days.

(21) Appl. No.: 09/533,317

(22) Filed: Mar. 22, 2000

(51) Int. Cl.[7] ............................................... A61N 1/18
(52) U.S. Cl. ...................................................... 607/32
(58) Field of Search .............................. 128/903; 607/4, 607/5, 9, 30, 32, 60; 600/301, 509, 300, 500, 503, 483; 340/517, 573.1, 825.06, 286.07

(56) References Cited

U.S. PATENT DOCUMENTS

| | | | | |
|---|---|---|---|---|
| 5,319,355 A | * | 6/1994 | Russek | 340/573 |
| 5,319,363 A | * | 6/1994 | Welch et al. | 340/825 |
| 5,634,468 A | * | 6/1997 | Platt et al. | 128/696 |
| 5,822,435 A | * | 10/1998 | Boebert et al. | 380/49 |
| 5,919,141 A | * | 7/1999 | Money et al. | 600/513 |
| 6,028,514 A | * | 2/2000 | Lemelson et al. | 340/539 |
| 6,057,758 A | * | 5/2000 | Dempsey et al. | 340/539 |

OTHER PUBLICATIONS

Selected Sections, including 5.3 ("Silencing Alarms"), from Operating Instructions for Siemens Sirecust 720/722/730/732 monitors, 4 pages, dated Mar. 1991.

Product literature describing controls and indicators of Physio–Control VSM 4 Vital Signs Monitor, 2 pages, (1986).

Selected pages, including p.2–2 describing "Alarm Silence Key," from Service Manual for Ohmeda Biox 3740 Pulse Oximeter, 3 pages, (1988).

Operating Instructions for Datascope Passport 5L, Rev. E, dated Nov. 1, 1996 (see pp. 2–2 and 2–3).

Operating Instructions for Datascope Visa Central Station, Rev. 2, dated Jul. 26, 1991.

* cited by examiner

*Primary Examiner*—Jeffrey R. Jastrzab
*Assistant Examiner*—Frances P. Oropeza
(74) *Attorney, Agent, or Firm*—Foley & Lardner; Carl B. Horton

(57) ABSTRACT

A medical telemetry system includes a procedure alarm silence feature that enables a clinician to remotely disable a monitoring station alarm in order to perform a patient procedure that might cause inadvertent false alarms. To disable the alarm for a preprogrammed time interval, the clinician presses keys on the telemetry unit according to a predefined key sequence that is selected so as to reduce a likelihood of accidental alarm disablement. The monitoring system responds to the predefined sequence by disabling an audible alarm for all alarm conditions except class 1 arrhythmias. A corresponding visual alarm at the monitoring station is maintained active. While the alarm is disabled, the monitoring station displays an indication of the amount of time until expiration of the preprogrammed time interval.

33 Claims, 1 Drawing Sheet

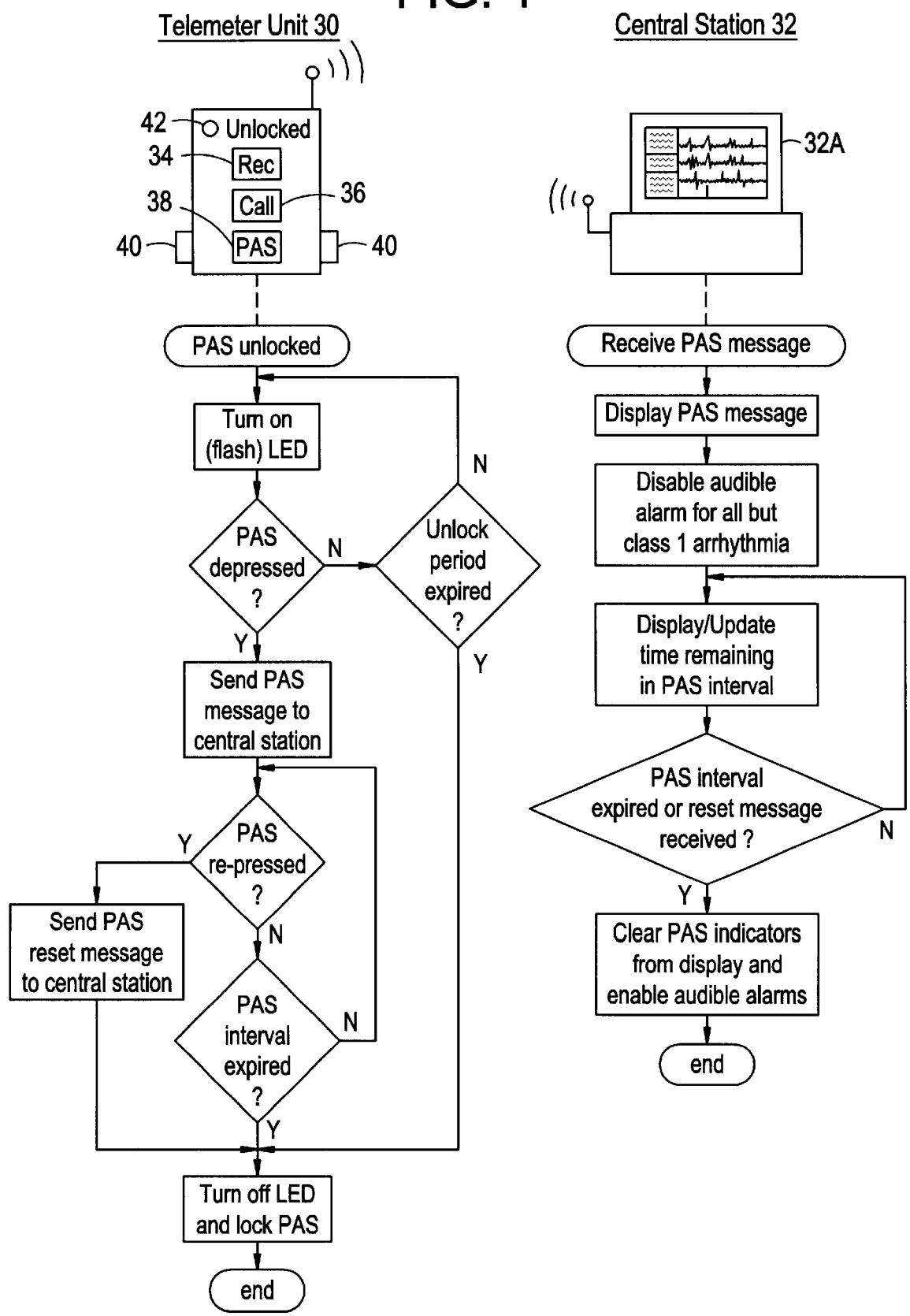

PROCEDURE ALARM SILENCE FEATURE FOR MEDICAL TELEMETRY SYSTEM

BACKGROUND OF THE INVENTION

A variety of medical telemetry systems exist which allow the ECG waveforms of hospital patients to be monitored in real time. The ECG signals of the patient are sensed by a telemeter unit and a set of ECG leads, and are transmitted by the telemeter unit to a monitoring station (typically located in a central location). In ambulatory systems, the telemeter units are battery-powered wireless units that are worn by the patients. The telemeter units may also be designed to sense and transmit other types of physiologic data such as pulse oximetry, non-invasive and invasive blood pressure, end tidal carbon dioxide, respiration, and temperature.

The monitoring station, which typically includes a PC or other computer system coupled to a receiver, displays the ECG waveforms of multiple patients for viewing by a human operator. The monitoring station also applies software-implemented analysis algorithms to check for abnormalities, such as arrhythmia conditions, high and low alarm limits, and lost signals caused by loose leads. When such an abnormality is detected, an alarm indicator is displayed on the screen, and/or an audible alarm is sounded.

SUMMARY OF THE INVENTION

One problem with existing medical telemetry systems is that false alarms frequently occur as the result of short-term procedures performed on the patients by nurses and other clinicians. For example, a false alarm may occur when a clinician replaces or repositions the ECG leads for patient. As a result, clinicians are unnecessarily dispatched to patients' rooms or otherwise distracted.

The present invention overcomes this problem by providing a "procedure alarm silence" feature through which a clinician can remotely disable the alarm from the bedside or other patient location for a predetermined time. The feature is preferably invoked by the clinician through a predefined sequence of key depressions or other actions on the telemeter unit. Once invoked, the monitoring station temporarily inhibits some or all types of alarms. In a preferred embodiment, for example, the monitoring station disables the audible alarm for a two minute interval for all monitored abnormalities except class 1 arrhythmia conditions. A corresponding visual alarm is preferably kept active. The predefined key sequence is preferably selected such that patients and clinicians are unlikely to invoke the feature (disable audible alarms) by accident.

BRIEF DESCRIPTION OF THE DRAWING

FIG. 1 illustrates the operation of an example telemeter unit and monitoring station according to the present invention.

DETAILED DESCRIPTION OF A PREFERRED EMBODIMENT

An example implementation of the invention will now be described with reference to FIG. 1, which is intended to illustrate but not limit the invention. The scope of the invention is defined by the appended claims.

As depicted in FIG. 1, the ambulatory telemeter units 30 (one shown) of the system include four types of buttons or keys: a Remote Record key 34, a Nurse Call key 36, a Procedure Alarm Silence (PAS) key 38, and a pair of Attendant Present/Procedure Alarm Silence Unlock keys 40 (preferably positioned on opposite sides of the telemeter unit). The functions performed by these keys are summarized in Table 1. The telemeter unit 30 also includes a "PAS Unlocked" LED 42 which flashes indicating that the PAS key is unlocked and can be actuated by pressing the PAS key. The keys illustrated in FIG. 1 are for illustrative purposes only, and are not intended to imply actual key sizes or locations.

The default state of the PAS key 38 is "locked" (non-functional). To unlock the PAS key, the clinician holds down both Attendant Present/Procedure Alarm Silence Unlock keys 40 until the "PAS unlocked" LED 42 begins flashing. As depicted by the telemeter flow diagram in FIG. 1, if the PAS key is not thereafter pressed within a preprogrammed "unlocked" period, the LED stops flashing and the PAS key is returned to the locked state. If, on the other hand, the PAS key is pressed while unlocked, a PAS message is sent to the central station 32 (monitoring system), causing the central station to enter into the PAS mode (audible alarms disabled, etc.) for the particular telemeter unit 30 and patient. The central station remains in the PAS mode with respect to that patient until expiration of a preprogrammed PAS interval, such as two minutes, or until the PAS key is re-pressed, whichever occurs first.

TABLE 1

| Key Type | Description |
| --- | --- |
| Remote Record | A dedicated function key that initiates a strip chart recording at the central (monitoring) station when depressed |
| Nurse Call | A dedicated function key that initiates a nurse call at the central station when depressed |
| Procedure Alarm Silence (PAS) | Used to inform clinicians at the central station area that the attending clinician will be performing a procedure that may cause inadvertent false alarms (changing lead wires, electrodes, etc.), and to disable audible (but not visual) alarms during the procedure. The PAS key performs no function unless unlocked. |
| Attendant Present/PAS Unlock | A multi-function key pair used for indicating that an attendant is present and for unlocking the PAS key. When both keys are pressed and held in for a preprogrammed time period, an "Attendant Present" indication is displayed at the central station. If the clinician continues to hold in both keys, a "PAS Unlock" indicator begins flashing to indicate that the PAS key is unlocked. |

As illustrated by the central station flow diagram, upon receiving the PAS message and entering into the PAS mode, the central station 32 disables the audible alarm for all but class 1 arrhythmia alarm conditions. The visual alarms preferably remain active. While in the PAS mode, a message such as "Temporary Procedure Alarm Silence Activated," and a visual indication of the amount of time remaining in the PAS interval, are displayed on a central station display screen 32A in association with the particular patient's data. Once either a "PAS Reset" message is received from the telemeter unit 30 (indicating a "PAS re-press" event) or the PAS interval expires, the PAS message and "time remaining" indicator are cleared from the display and the audible alarms are re-enabled.

As will be apparent from the foregoing, any of a variety of alternative key types and key depression sequences could be used to remotely disable the alarms. In addition, other types of clinician actions could be used to initiate the PAS mode, such as applying a magnetic or electronic key to the telemeter unit. Further, although the feature is illustrated in connection with a wireless, ambulatory telemeter unit, the feature may be incorporated into hardwired and other non-ambulatory telemeter units.

What is claimed is:

1. In a system in which physiologic data of a patient is sensed and transmitted to a monitoring station by an ambulatory telemeter unit worn by the patient, and in which the monitoring station analyzes the physiologic data in real time to check for alarm conditions, a method of remotely disabling an alarm of the monitoring station, comprising:

detecting a predefined user action performed on the ambulatory telemeter unit worn by the patient; and responding to detection of the predefined user action by transmitting a message from the ambulatory telemeter unit to the monitoring station to cause the monitoring station to preemptively disable an alarm at the monitoring station for a preprogrammed time period, to thereby inhibit false alarms as a procedure is performed on the patient.

2. The method as in claim 1, wherein the predefined user action is selected to reduce a likelihood that the alarm will be disabled by the patient.

3. The method as in claim 1, wherein the predefined user action comprises a sequence of key depressions in which an alarm silencing function is unlocked and then activated.

4. The method as in claim 1, wherein the predefined user action comprises applying an electronic or magnetic key to the ambulatory telemeter unit.

5. The method as in claim 1, wherein the predefined user action comprises a predefined sequence of key depressions on the ambulatory telemeter unit, the predefined sequence of key depressions selected so as to reduce a likelihood that the alarm will be disabled by accident.

6. The method as in claim 5, wherein the predefined sequence of key depressions requires at least two keys to be held in a depressed state simultaneously.

7. The method as in claim 1, wherein the message causes the monitoring station to disable an audible alarm without disabling a corresponding visual alarm.

8. The method as in claim 1, wherein the message causes the monitoring station to disable the alarm for some, but not all, types of alarm conditions.

9. The method as in claim 8, wherein the monitoring station responds to the message by maintaining the alarm in an active state for class 1 arrhythmia conditions.

10. The method as in claim 1, further comprising displaying at the monitoring station an indication that an alarm associated with the ambulatory telemeter unit is currently disabled.

11. The method as in claim 1, further comprising displaying at the monitoring station an indication of an amount of time left until expiration of the preprogrammed time period.

12. The method as in claim 1, further comprising enabling the alarm prior to expiration of the preprogrammed time period in response to detection of a second predefined user action performed on the ambulatory telemeter unit.

13. A medical telemetry system, comprising:

an ambulatory telemeter unit that senses and transmits physiologic data of a patient in real time, the ambulatory telemeter unit configured to be worn by the patient; and a monitoring system that receives and displays the physiologic data transmitted by the ambulatory telemeter unit, and analyses the physiologic data to check for at least one type of alarm condition;

wherein the monitoring system is responsive to a predefined user action performed on the ambulatory telemeter unit by preemptively disabling an alarm associated with the ambulatory telemeter unit for a preprogrammed time interval, so that a clinician can remotely disable the alarm while performing a procedure on the patient.

14. The system as in claim 13, wherein the monitoring system responds to the predefined user action by disabling an audible alarm without disabling a corresponding visual alarm.

15. The system as in claim 13, wherein the monitoring system responds to the predefined user action by disabling the alarm for some, but not all, types of alarm conditions.

16. The system as in claim 15, wherein the monitoring system maintains the alarm in an active state during the preprogrammed time interval for class 1 arrhythmia alarm conditions.

17. The system as in claim 13, wherein the monitoring system further responds to the predefined user action by displaying an indication that the alarm associated with the ambulatory telemeter unit is currently disabled.

18. The system as in claim 13, wherein the monitoring system further responds to the predefined user action by displaying an amount of time left until expiration of the preprogrammed time interval.

19. The system as in claim 13, wherein the predefined user action comprises a predefined sequence of key depressions on the ambulatory telemeter unit.

20. The system as in claim 19, wherein the predefined sequence of key depressions is selected so as to reduce a likelihood that the alarm will be disabled by accident.

21. The system as in claim 20, wherein the predefined sequence of key depressions requires at least two keys to be held in a depressed state simultaneously.

22. The system as in claim 13, wherein the predefined user action comprises applying a key to the ambulatory telemeter unit.

23. The system as in claim 13, wherein the monitoring system is responsive to a second type of user action performed with respect to the ambulatory telemeter unit by enabling the alarm prior to expiration of the preprogrammed time interval.

24. A telemeter unit, comprising:

a housing having a plurality of keys;

a lead set that attaches to a patient to sense physiologic data of the patient, wherein the telemeter unit is configured to transmit the physiologic data to a remote monitoring station; and a processing module which is responsive to a predefined sequence of depressions of the keys by transmitting an alarm silencing message to the remote monitoring station to cause the remote monitoring station to preemptively disable an alarm associated with an automated analysis of the physiologic data, the predefined sequence of depressions selected to reduce a likelihood that the alarm will be disabled by accident.

25. The telemeter unit as in claim 24, wherein the predefined sequence of depressions comprises a first action that causes an alarm silencing function to become unlocked for a predefined time period, followed by a second action performed within the predefined time period.

26. The telemeter unit as in claim 25, wherein the processing module is responsive to the first action by visually indicating to a user that the alarm silencing function is in an unlocked state.

27. The telemeter unit as in claim 24, wherein the predefined sequence of key depressions requires at least two of the keys to be held in a depressed state simultaneously.

28. The telemeter unit as in claim 24, wherein the telemeter unit is adapted to be worn by the patient while ambulatory.

29. The method as in claim 1, wherein the predefined user action comprises a first sub-action that causes an alarm silencing function to become unlocked for a predefined time period, followed by a second sub-action performed within the predefined time period.

30. The method as in claim 29, wherein the first sub-action comprises maintaining two keys of the ambulatory telemeter unit in a depressed state simultaneously.

31. The medical telemetry system as in claim 13, wherein the predefined user action comprises a first sub-action that causes an alarm silencing function to become unlocked for a predefined time period, followed by a second sub-action performed within the predefined time period.

32. The medical telemetry system as in claim 31, wherein the first sub-action comprises maintaining two keys of the ambulatory telemeter unit in a depressed state simultaneously.

33. A medical telemetry system, comprising;

an ambulatory telemeter unit that senses and transmits physiologic data of a patient in real time, the ambulatory telemeter unit configured to be worn by the patient; and a monitoring system that receives and displays the physiologic data transmitted by the ambulatory telemeter unit, and analyses the physiologic data to check for at least one type of alarm condition;

wherein the telemetry system is responsive to a predefined user action performed on the ambulatory telemeter unit by disabling an alarm associated with the ambulatory telemeter unit prior to an expected alarm condition for a preprogrammed time interval, so that a clinician can remotely disable the alarm while performing a procedure on the patient.

* * * * *